(12) United States Patent
Mitteldorf (10) Patent No.: US 9,168,002 B2
(45) Date of Patent: Oct. 27, 2015

(54) DEVICE AND METHOD FOR MEASURING RADIATION EXPOSURE

(71) Applicant: Malecare, Inc., New York, NY (US)

(72) Inventor: Darryl Mitteldorf, New York, NY (US)

(73) Assignee: Malecare, Inc., New York, NY (US)

( * ) Notice: Subject to any disclaimer, the term of this patent is extended or adjusted under 35 U.S.C. 154(b) by 256 days.

(21) Appl. No.: 13/830,188

(22) Filed: Mar. 14, 2013

(65) Prior Publication Data

US 2014/0275939 A1    Sep. 18, 2014

(51) Int. Cl.
*A61N 5/10* (2006.01)
*A61B 6/00* (2006.01)
*G01T 1/02* (2006.01)
*A61B 5/00* (2006.01)

(52) U.S. Cl.
CPC ............ *A61B 5/6804* (2013.01); *A61B 5/6802* (2013.01); *A61B 5/6813* (2013.01); *A61B 6/4275* (2013.01); *A61B 6/46* (2013.01); *A61B 6/42* (2013.01); *A61B 6/4266* (2013.01); *A61N 5/1071* (2013.01); *G01T 1/02* (2013.01); *G01T 1/026* (2013.01)

(58) Field of Classification Search
CPC . A61N 5/1048; A61N 5/1071; A61N 5/1075; A61N 5/68; A61N 5/6801; A61N 5/6802; A61N 5/6803; A61N 5/6804; A61N 5/6813; A61N 5/6814; A61N 5/6823; A61N 5/6843; A61N 5/6844; A61B 6/42; A61B 6/4208; A61B 6/4266; A61B 6/4275; A61B 6/46; A61B 6/50; A61B 6/501; A61B 6/502; A61B 6/503; A61B 19/54; A61B 19/5466; A61B 5/68; A61B 5/6801; A61B 5/6802; A61B 5/6803; A61B 5/6804; A61B 5/6813; A61B 5/6814; A61B 5/6823; A61B 5/6843; A61B 5/6844; G01T 1/02; G01T 1/023; G01T 1/026; G01T 1/20; G01T 1/203; G01T 1/2033; G01T 1/24; G01T 1/2928; H05G 1/26; H05G 1/28
USPC ............ 378/63, 91, 162, 165, 189, 204, 208, 378/210; 250/361 R, 362, 363.01, 363.02, 250/363.08, 370.01, 370.11, 370.12, 250/370.14, 371
See application file for complete search history.

(56) References Cited

U.S. PATENT DOCUMENTS 4,365,341 A     12/1982  Lam
5,444,254 A  *  8/1995   Thomson ................. 250/370.07

(Continued)

OTHER PUBLICATIONS

Street et al., "Jet-printing of Active-Matrix TFT Backplanes for Displays and Sensors," *IS&T Reporter—The Window on Imaging*, 20(5):1-4, (2005).

(Continued)

*Primary Examiner* — Anastasia Midkiff
(74) *Attorney, Agent, or Firm* — Alston & Bird LLP (57) ABSTRACT

Garments and methods for monitoring radiation exposure and cumulative radiation exposure in individuals undergoing repeated exposure to ionizing radiation are disclosed.

19 Claims, 6 Drawing Sheets

(56) References Cited

U.S. PATENT DOCUMENTS

| | | | |
|---|---|---|---|
| 6,260,202 B1 | 7/2001 | Villalobos et al. | |
| 6,395,121 B1 | 5/2002 | De Bastiani | |
| 6,438,202 B1 | 8/2002 | Olivera et al. | |
| 7,557,353 B2 | 7/2009 | Black et al. | |
| 7,563,026 B2 | 7/2009 | Mandelkern et al. | |
| 7,891,019 B2 | 2/2011 | Goldfine | |
| 2002/0087101 A1* | 7/2002 | Barrick et al. | 600/587 |
| 2005/0242289 A1 | 11/2005 | Grichnik et al. | |
| 2006/0027756 A1 | 2/2006 | Thomson et al. | |
| 2007/0089800 A1* | 4/2007 | Sharma | 139/388 |
| 2012/0146784 A1* | 6/2012 | Hines et al. | 340/539.11 |
| 2013/0274587 A1* | 10/2013 | Coza et al. | 600/409 |
| 2014/0135593 A1* | 5/2014 | Jayalth et al. | 600/301 |

OTHER PUBLICATIONS

Street et al., "Printed active-matrix TFT arrays for x-ray imaging (Invited Paper)," *SPIE*, Conference Procedings, Medical Imaging 2005: Physics of Medical Imaging, vol. 5745, abstract (2005). [Retrieved from the Internet Mar. 14, 2013: <URL: http://proceedings.spiedigitallibrary.org/proceeding.aspx?articleid=860621>].

\* cited by examiner

DEVICE AND METHOD FOR MEASURING RADIATION EXPOSURE

FIELD OF THE INVENTION

The invention lies in the field of medicine, and in particular the detection and measurement of ionizing radiation and accumulated radiation exposure.

BACKGROUND OF THE INVENTION

Exposure to ionizing radiation (e.g., x-rays) is a frequent component of diagnostic and therapeutic procedures in modern medicine. Although the precision of instruments used in such procedures continues to improve, individuals undergoing diagnostic or therapeutic procedures utilizing ionizing radiation are commonly exposed to at least some stray radiation that inadvertently contacts other parts of the body.

Because medical diagnostic and therapeutic procedures are often ordered and performed by different physicians and/or different facilities over extended periods of time (e.g., years) and are often directed to different parts of an individual's body, it becomes increasingly difficult for the individual to know or maintain a record of accumulated radiation exposure, particularly with reference to specific parts of the body.

SUMMARY OF THE INVENTION

In one aspect, the present invention relates to a garment, comprising (i) an array of radiation sensitive devices, and (ii) a fabric-based flexible circuit electrically coupled to the array of radiation sensitive devices, wherein the garment is shaped to be worn by an individual and to cover all or substantially all of the individual's body or part thereof. In some cases, the garment is shaped to cover the individual's entire body excluding the face, hands and feet. In some cases, the garment is in the shape of a T-shirt and covers the individual's torso. In some cases, the garment is shaped to further cover the individual's arms. In some cases, the garment is in the shape of shorts and covers the individual's pelvis. In some cases, the garment is in the shape of pants and covers the individual's pelvis and legs.

In some embodiments, the fabric-based flexible circuit comprises a conductive ink printed on a polymer or nylon fabric in a predetermined circuit pattern. In some cases, the fabric-based flexible circuit comprises a fabric substrate that is transparent or substantially transparent to ionizing radiation.

In some embodiments, each radiation sensitive device is from 5 to 50 µm in diameter or width (e.g., the device may be from 25 µm² to 2.5 mm²). In some cases, each radiation sensitive device is from 10 to 40 µm in diameter or width, or preferably about 25 µm in diameter or width (e.g., about 625 µm²). In some cases, each radiation sensitive device is from 250 µm² to 1 mm² in size. In some cases, the radiation sensitive devices comprise MOSFET, RADFET or IGFET semiconductor components. In some cases, the radiation sensitive devices comprise flat panal detectors.

In some embodiments, the array of radiation sensitive devices comprises at least one device per 100 cm². In some cases, the array comprises at least one device per 50 cm². In some cases, the array comprises at least one device per 25 cm², at least one device per 10 cm², at least one device per 5 cm², or at least one device per 1 cm².

In some embodiments, the garment further comprises a plurality of markers positioned at predetermined locations relative to the array of radiation sensitive devices. In some cases, the markers are identifiable in a digital image of the garment when worn by the individual.

In some embodiments, the garment is shaped to fit snugly against the individual's body when worn. In some cases, the array of radiation sensitive devices and the flexible circuit form an integrated internal layer, and the garment further comprises an external layer connected to the internal layer to form an inflatable space therebetween, wherein the space can be inflated with air when worn by the individual.

In some embodiments, the garment further comprises a data collection device electically coupled to the flexible circuit to receive and store radiation data.

In another aspect, the present invention comprises a garment having a plurality of pockets and a plurality of radiation sensitive devices contained in the plurality of pockets, wherein the garment is shaped to be worn by an individual and to cover all or substantially all of the individual's body or part thereof.

In another aspect, the present invention comprises a method of monitoring radiation exposure in an individual undergoing a radiation diagnostic or treatment session, in which the method comprises (i) supplying an individual with a garment as discussed above and herein, (ii) administering radiation to the individual, and recording the radiation incident on the radiation sensitive devices. In some cases, the method further comprises taking a digital photograph of the individual wearing the garment prior to, during, or after radiation exposure to identify the location of one or more markers. In some cases, the method further comprises calculating a cumulative radiation exposure for the individual or a part of the individual's body.

The details of additional embodiments of the invention are set forth in the description below. Any or all of the features discussed above and throughout the application can be combined in various embodiments of the present invention. Other features and advantages of the invention will be apparent from the detailed description and the accompanying drawings, and from the claims.

BRIEF DESCRIPTION OF THE DRAWINGS

FIGS. 1A-1D are illustrations showing various garments in accordance with embodiments of the invention.

DETAILED DESCRIPTION OF THE INVENTION

I. General

As an overview, the present invention relates to garments and methods for monitoring radiation exposure and cumulative radiation exposure in individuals, e.g., patients undergoing repeated diagnostic or therapeutic procedures (e.g., CT scans or radiotherapy) using ionizing radiation (e.g., x-rays). The garments of the present invention are designed to be, or to be made to be (e.g., via inflation) form fitting or substantially form fitting such that the location of the radiation sensitive devices on or in the garment can be correlated to specific locations of the individual's body. In this manner, the dose of radiation incident upon particular parts (e.g., specific organs) of the individual's body can be measured and a record maintained of cumulative exposure over time. Methods of the present invention provide a procedure for monitoring radiation exposure by collecting data of the radiation dose received at each radiation sensitive device on or in a garment worn by an individual during a session in which the individual is exposed to radiation, and maintaining a record of cumulative exposure over time.

Embodiments of garments and methods for measuring radiation exposure or cumulative radiation exposure are described in detail herein. In the following description, numerous specific details are identified to provide a thorough understanding of embodiments of the invention. One skilled in the art will recognize, however, that the invention can be practiced without one or more of the specific details, or with other methods, components, materials, etc. without departing from the invention. In some instances, well-known components or operations are not shown or described in detail to avoid obscuring aspects of various embodiments of the present invention.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more embodiments.

II. Garments

Garments useful in accordance with the present invention may be made of any durable flexible material or fabric that can be fashioned into the form of a one-piece or multi-piece article of clothing, e.g., in the form of a shirt, T-shirt, pants, shorts, socks, gloves, hood, sleeveless vest and/or combinations of the foregoing. For example, the garments may be made from woven polymer materials such as polyester or nylon fabric, cotton, or the like. In some cases, the material is selected to be transparent or substantially transparent to ionizing radiation. The garments may be manufactured in different sizes/cuts to fit or conform to any of various body sizes and shapes.

Figure 1A:
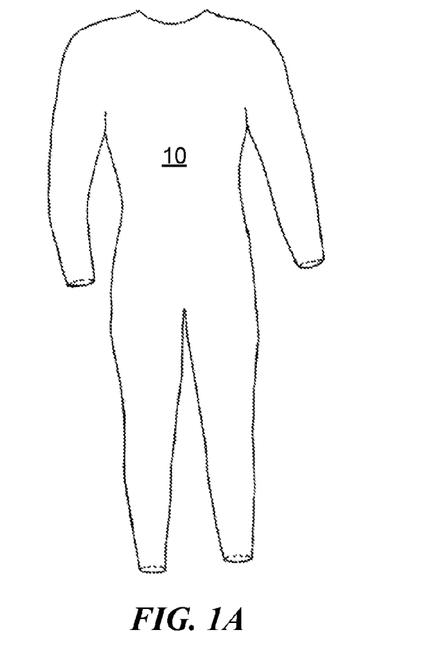
FIG. 1A shows a garment that covers an individual's entire body, excluding the feet, hands, neck and head.
Figure 1B:
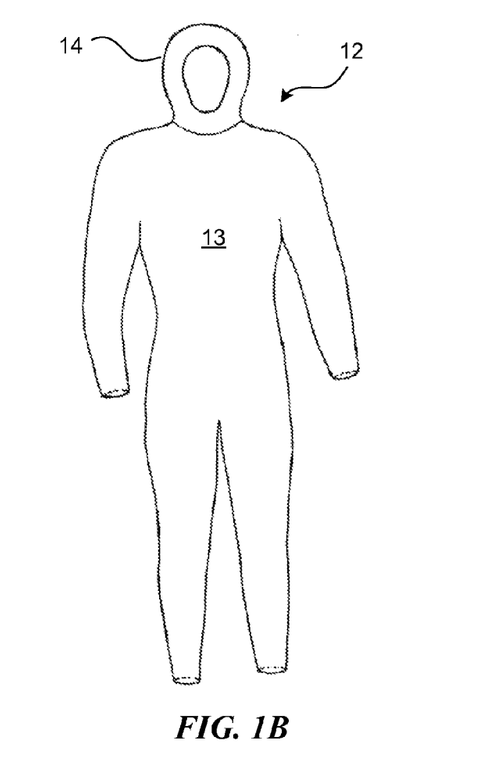
FIG. 1B shows a garment that covers an individual's entire body, excluding the face, hands and feet.
Figure 1C:
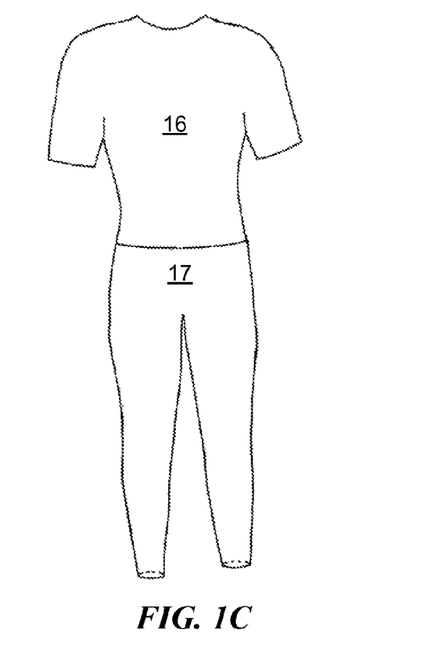
FIG. 1C shows a pair of garments, the first in the shape of a T-shirt and the second in the shape of pants.
Figure 1D:
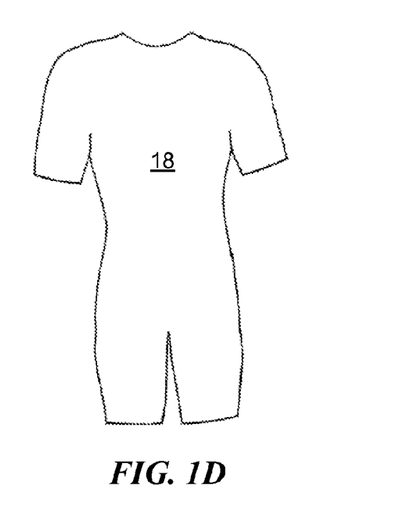
FIG. 1D shows a garment that covers an individual's torso and pelvis.
Figures 2A, 2B:
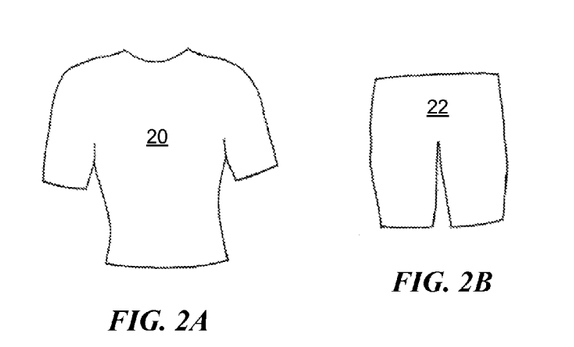
FIGS. 2A-2E are illustrations showing individual garments in the shape of a T-shirt" 20 (FIG. 2A), shorts 22 (FIG. 2B), a hood 24 (FIG. 2C), socks 26 (FIG. 2D), and gloves 28 (FIG. 2E) in accordance with embodiments of the invention.
Figure 2C:
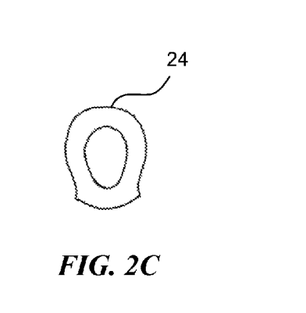
Figures 2D, 2E:
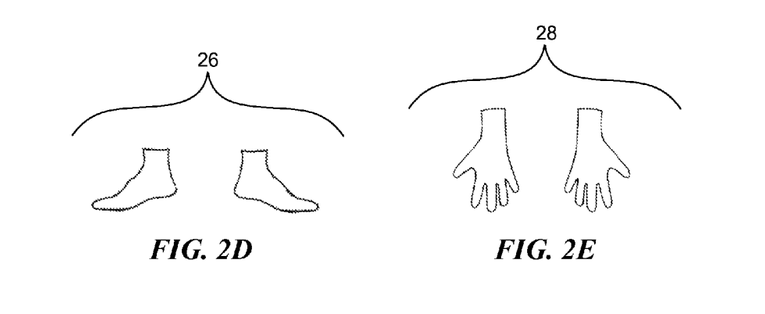

Selection of a garment or garments to cover particular parts of an individual's body will depend on the location of the body to which radiation is expected to be directed. For example, if a chest x-ray is to be taken, one may select a garment or garments to cover the individual's torso, pelvis and head to measure stray radiation incident on these portions of the body during the chest x-ray. FIGS. 1A-1D and 2A-2E show various garments in accordance with embodiments of the present invention. In FIG. 1A, a one-piece body suit 10 is illustrated, which could be used to cover an individual's entire body, excluding the feet, hands, neck and head. In FIG. 1B, a hooded body suit 12 is illustrated, which includes a body suit 13, as in FIG. 1A, and a hood 14, which may be integrated with the remainder of the body suit 13 or be a separate article. In FIG. 1C, a two-piece body suit is illustrated, which includes a "T-shirt" 16 and "pants" 17 to cover an individual's torso and lower body, excluding the feet. In FIG. 1D, a one-piece body suit 18 is illustrated, which could be used to cover an individual's torso and pelvis.

For measuring doses of incident radiation at various body locations, the garments of the present invention include a plurality of radiation sensitive devices located at various positions on the garment. In some cases, the radiation sensitive devices are located on all surfaces of the garment, i.e., the front, back and sides. In other cases the radiation sensitive devices are located on only the front and sides, the back and sides, only the front, only the back, or only a side or both sides of the garment.

A. Radiation Detectors

Radiation sensitive devices (or radiation detectors) useful in accordance with the present invention comprise components capable of converting ionizing radiation (e.g., X-rays) to an electrical signal that can be measured. In one embodiment, the radiation sensitive device comprises a scintillation element optically coupled to a detector element. The scintillation element can comprise any material capable of converting ionizing radiation to visible wavelengths, e.g., inorganic materials such as cesium iodide or gadolinium oxysulfide.

In some cases, the scintillation element comprises material selected from inorganic compounds such as cesium iodide, thallium-doped sodium iodide, cesium fluoride, thallium-doped potassium iodide, europium-doped lithium iodide, barium fluoride, europium-doped calcium fluoride, silver-doped zinc sulfide, gadolinium oxysulfide, or other known scintillation compounds. In some cases, the scintillation element comprises material selected from organic compounds or plastics such as polyethylene naphthalate. In some cases, the scintillation element is a flexible plastic or polymeric material that is doped with an inorganic scintillating material such as cesium iodide.

In some cases, the detector element comprises a thin film transistor or thin film transistor array, a charge-coupled device, a CMOS (complementary metal-oxide-semiconductor) element, a metal-oxide field effect transistor (MOSFET), an insulated-gate field-effect transistor (IGFET), a radiation-sensing field effect transistor (RADFET), or an array of MOSFET, RADFET or IGFET transistors.

Figure 3A:
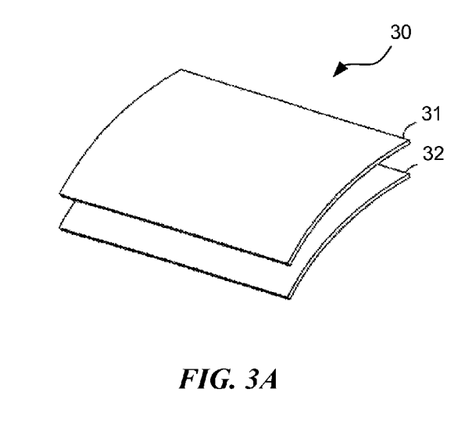
FIGS. 3A and 3B are illustrations of layered radiation sensitive devices in accordance with embodiments of the invention.
Figure 3B:
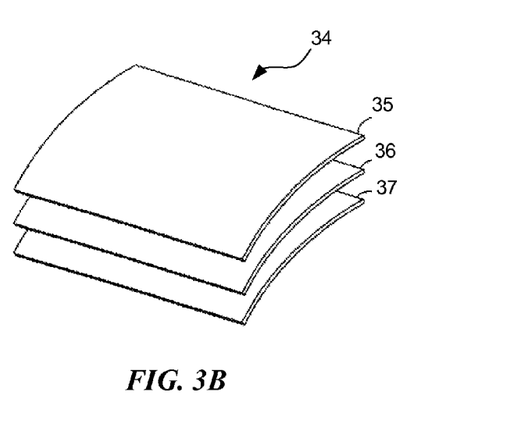

With reference to FIGS. 3A and 3B, the radiation sensitive device can, in various embodiments, comprise two or three or more layered elements that convert ionizing radiation (e.g., x-rays or gamma rays) to a measureable electrical signal (e.g., a digital signal). In one embodiment, as shown in FIG. 3A, the radiation sensitive device 30 comprises a first layer 31, which may be a scintillation element comprising, for example, a flexible material doped with a scintillating compound such as cesium iodide or amorphous selenium, and a second layer 32, which may be a detector element comprising, for example, a flexible thin film transistor or thin film transistor array. In an alternate embodiment, as shown in FIG. 3B, the radiation sensitive device 34 comprises a first layer 35, which may be a scintillation element comprising, for example, a flexible material doped with a scintillating compound (e.g., cesium iodide), a second layer 36, which may be a photodiode layer (e.g., amorphous silicon) that converts the photons from the scintillation layer to an electrical charge, and a third layer 37, which may be a detector element comprising, for example, a flexible thin film transistor or thin film transistor array. In some cases the detector element is a CCD or CMOS element.

In some embodiments, the radiation detectors comprise printed radiation sensitive devices, as discussed in, e.g., Street et al., *IS&T Reporter*, 20(5):1-4 (2005). Printed radiation detectors can be miniaturized to reduce or avoid interference with the overall diagnostic or therapeutic objectives of the radiation. In various embodiments, the radiation detectors are from 25 $\mu m^2$ to 2.5 $mm^2$ in size or from 250 $\mu m^2$ to 1 $mm^2$ in size. In some cases, the radiation detectors are 25 $\mu m^2$, 50 $\mu m^2$, 75 $\mu m^2$, 100 $\mu m^2$, 150 $\mu m^2$, 200 $\mu m^2$, 250 $\mu m^2$, 300 $\mu m^2$, 350 $\mu m^2$, 400 $\mu m^2$, 450 $\mu m^2$, 500 $\mu m^2$, 550 $\mu m^2$, 600 $\mu m^2$, 650 $\mu m^2$, 700 $\mu m^2$, 750 $\mu m^2$, 800 $\mu m^2$, 850 $\mu m^2$, 900 $\mu m^2$, 950 $\mu m^2$, 1 $mm^2$, 1.5 $mm^2$, 2 $mm^2$, 2.5 $mm^2$, 3 $mm^2$, 3.5 $mm^2$, 4 $mm^2$, 4.5 $mm^2$, 5 $mm^2$, 5.5 $mm^2$, 6 $mm^2$, 6.5 $mm^2$, 7 $mm^2$, 7.5 $mm^2$, 8 $mm^2$, 8.5 $mm^2$, 9 $mm^2$, 9.5 $mm^2$, or 10 $mm^2$ in size. Ranges of values using any combination of any of the above-recited values as upper and/or lower limits are also intended to be included herein.

In preferred embodiments, the garment comprises an array of radiation detectors. The number of radiation detectors and their density on the garment can be adjusted depending on the surface area of the body that will be exposed to the radiation, and the desired precision with respect to the exposed area. For example, if the individual is being exposed to a relatively uniform field of radiation over the entire body (e.g., a diagnostic CT scan), a small number of detectors (e.g., 1 detector per 100 $cm^2$ or 1 detector per 500 $cm^2$) may be used as the exposure of particular portions of the body will be relatively uniform. In instances in which only a portion of the body is being exposed (e.g., radiation therapy directed at a tumor), or the exposed area includes a relatively larger number of different organs (e.g., the abdomen), it is preferable to use a greater density of detectors (e.g., 1 detector per 10 $cm^2$ or 1 detector per $cm^2$) with more precisely known locations relative to particular body parts.

In some cases, the detectors are arranged in a uniform pattern on the garment. In some cases, an array of radiation detectors includes at least one device per 500 $cm^2$, at least one device per 400 $cm^2$, at least one device per 300 $cm^2$, at least one device per 200 $cm^2$, at least one device per 100 $cm^2$, at least one device per 90 $cm^2$, at least one device per 80 $cm^2$, at least one device per 70 $cm^2$, at least one device per 60 $cm^2$, at least one device per 50 $cm^2$, at least one device per 40 $cm^2$, at least one device per 30 $cm^2$, at least one device per 20 $cm^2$, at least one device per 10 $cm^2$, at least one device per 5 $cm^2$, or at least one device per 1 $cm^2$. Ranges of values using any combination of any of the above-recited values as upper and/or lower limits are also intended to be included herein.

B. Wiring

Figure 4:
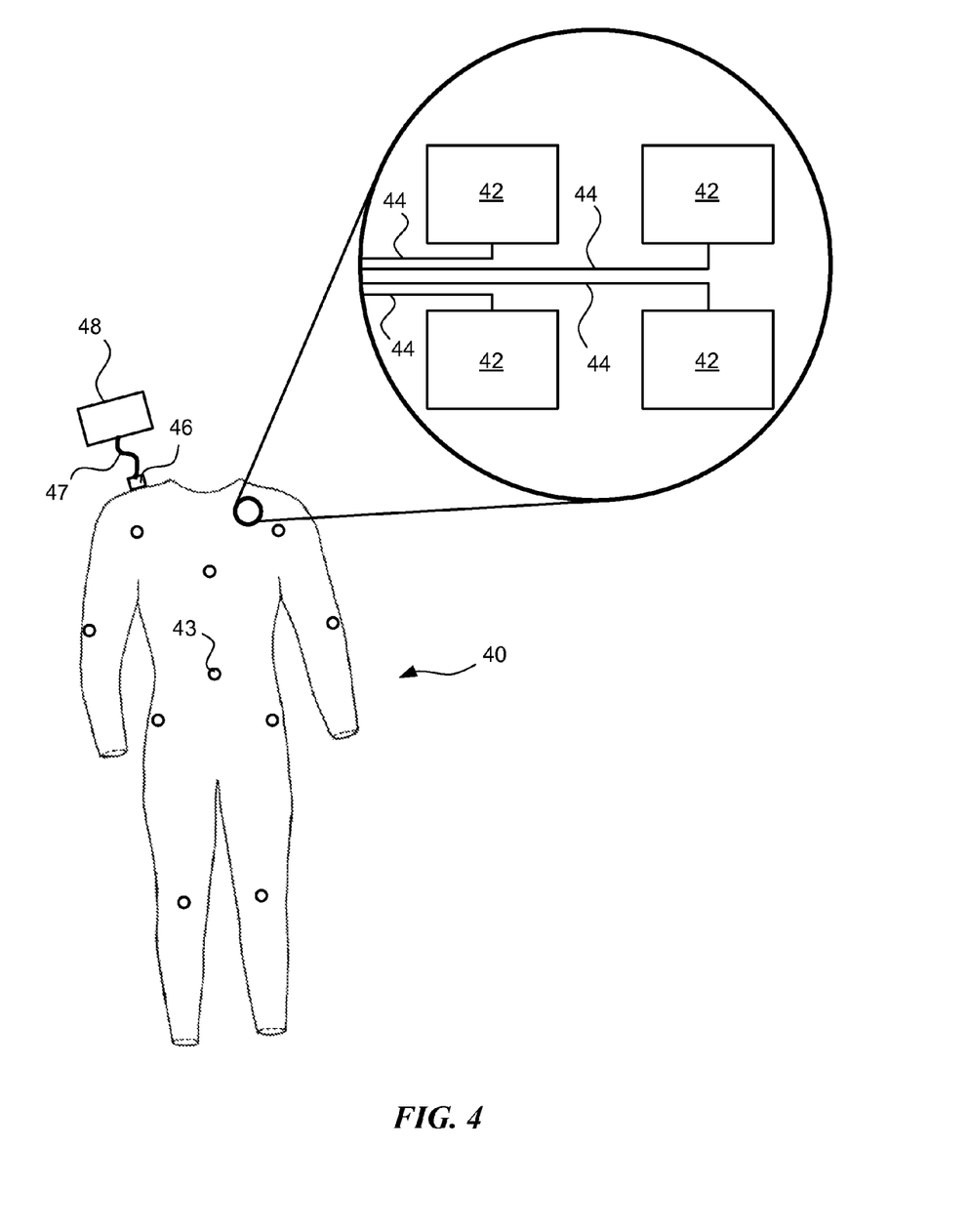
FIG. 4 is an illustration showing a garment with a plurality of markers, an enlarged view of radiation sensitive devices and flexible wiring on the garment, and an electrically coupled data collection device in accordance with an embodiment of the invention.

The radiation sensitive devices can be electrically coupled to an electronic circuit, or a port to which an electronic circuit can be attached, in order to measure the electrical signal generated from each detector element as a result of the incident radiation. With reference to FIG. 4, an exemplary garment 40 comprises a plurality of radiation detectors 42, a subset of which are shown in the enlarged view, electrically coupled via wires 44 to an external port or electronic sensor unit 46, which may be integrated into the garment. In some cases, the port or electronic sensor unit 46 may be electrically coupled to a computer or other electronic device 48 via, e.g., a cable 47 to upload or otherwise read or monitor the electrical signals generated from the radiation detectors 42 in response to incident radiation. In some cases, the electronic device 48 includes a battery or other power source to operate the detectors. In some cases, the power source is provided separately (e.g., via a battery or batteries positioned on or in the garment and electrically connected to the detectors) from the electronic device that monitors the electrical signals generated from the radiation detectors. In the illustrated embodiment, the garment also includes a plurality of markers 43, which are discussed in greater detail below.

In some embodiments, the wires 44 may comprise a flexible circuit of conductive ink printed onto the fabric or other material from which the garment is made. In some cases, the circuit is printed in a predetermined pattern on the material from which the garment will be produced in order to provide connections for a predetermined number of radiation detectors that are or will be attached or deposited onto the garment. Thus, in some embodiments both the radiation detectors and the wiring to connect the detectors to an external port or electronic sensor unit are printed onto the garment or onto the material from which the garment is made.

Figure 5:
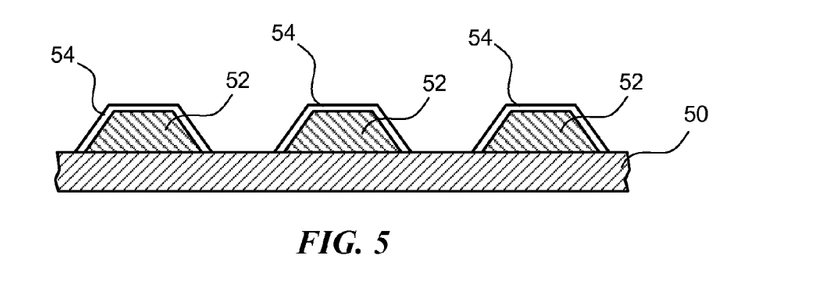
FIG. 5 is an illustration showing a cross-sectional view of a flexible printed circuit in accordance with an embodiment of the invention.

As shown in FIG. 5, which is a cross-sectional view of a flexible printed circuit, flexible conductive ink 52 is printed or deposited onto a flexible substrate 50, which is, e.g., a fabric or other material from which a garment can be made, and can, in some cases, include a protective coating 54 over the conductive ink. Both the conductive ink and the protective coating can be applied to the fabric or other material using commonly known screen printing techniques.

Figure 6:
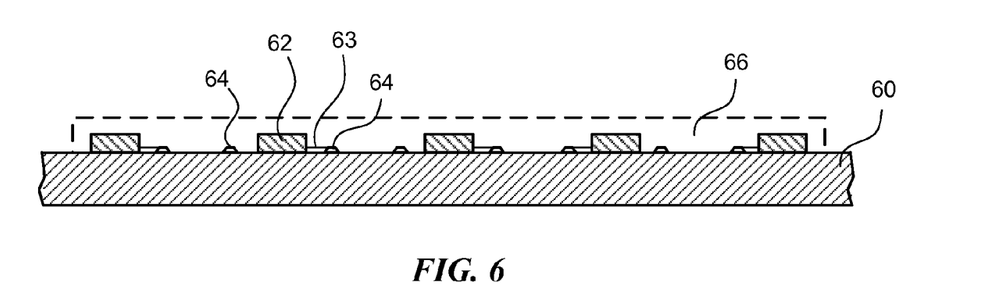
FIG. 6 is an illustration showing a cross-sectional view of fabric with radiation sensitive devices and wiring layered thereon in accordance with an embodiment of the invention.

With reference now to FIG. 6, a cross-sectional view of a flexible substrate (e.g., fabric) 60 is shown with a plurality of radiation sensitive devices 62 and a flexible circuit 64 attached or deposited onto the surface of the substrate. The flexible circuit 64 includes flexible wiring 63 electrically connecting the radiation sensitive devices 62 to the flexible circuit 64. In some embodiments, the radiation sensitive devices and the flexible circuit are optionally covered by a second flexible material 66, e.g., a fabric, to provide a protective barrier against damage to the radiation detectors and the electronic circuit. Preferably, the second material is completely or substantially transparent to ionizing radiation (e.g., x-rays).

C. Inflatable Layer

Figure 7:
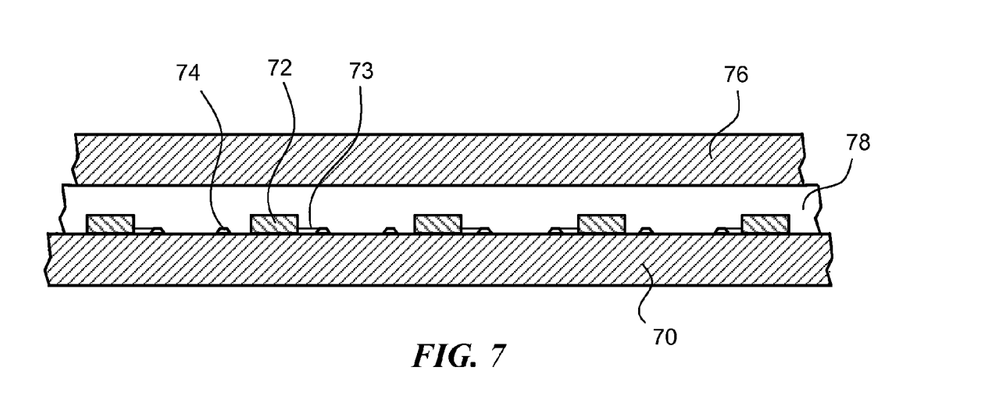
FIG. 7 is an illustration showing a cross-sectional view of layered fabric forming an inflatable space in accordance with an embodiment of the invention.

In some cases, the garments of the present invention are form fitting, or can be made to be form fitting or substantially form fitting by inflation of a portion of the garment. With reference to FIG. 7, a cross-sectional view of a portion of a garment is shown, which includes a flexible substrate 70 with a plurality of radiation sensitive devices 72 and a flexible circuit 74 mounted or deposited thereon, and including wiring 73 electrically coupling the radiation detectors to the flexible circuit, a flexible barrier layer 76, and an inflatable layer 78 positioned between the flexible substrate and the flexible barrier. In another embodiment, the flexible barrier layer is optional or comprises only the outer edge of the inflatable layer 78. Preferably, both the inflatable layer and the optional barrier layer are made of materials that are transparent or substantially transparent to ionizing radiation (e.g., x-rays).

In an embodiment, the inflatable layer includes a inlet tube (not shown) for introducing air or other gas into the inflatable layer to thereby make the garment, and the flexible substrate in particular, fit closely against the wearer's skin so that the radiation sensitive devices (and the optional markers) are held firmly in place relative to the wearer's body or relative to specific locations (e.g., marker locations) of the wearer's body.

D. Markers

With reference again to FIG. 4, a plurality of markers 43 can be included in various embodiments of the present invention. The markers can be located at various positions relative to positions of the body and/or relative to the locations of the plurality of radiation sensitive devices. In some cases, the markers are made of a material that is impermeable to ionizing radiation, e.g., lead, so that the locations of the markers can be determined relative to internal organs in, e.g., an x-ray image of an individual wearing the garment with the markers. The relative locations of the markers with respect to portions of the wearer's body can also be determined using a digital image of the individual wearing the garment comprising the markers. In such cases, the markers are identifiable in the digital image.

In various embodiments, the markers are from 1 mm in diameter to 5 mm or 10 mm in diameter. In some cases, the markers are located at or near distinct portions of the individual wearer's body, for example, at one or more of the navel, center of chest, underarms, elbows, hips and knees as shown in FIG. 4. The markers can also be located at other locations relative to the wearer's body, and the number of markers can be adjusted for density, as discussed above in connection with the radiation detectors. In some cases, the markers are removable such that an image can be obtained with the markers located on the garment, followed by removal of the markers prior to exposure of the wearer to the diagnostic or therapeutic radiation.

The markers, whether or not removable, can be located on the garment in known locations relative to the radiation detectors or a subset of the radiation detectors. In the latter case, different markers may have known locations relative to various subsets of detectors and in some cases the subsets may overlap (e.g., two different markers have known locations relative to the same detector). This allows for more precise correlation of radiation exposure to particular parts of the individual's body.

Figure 8:
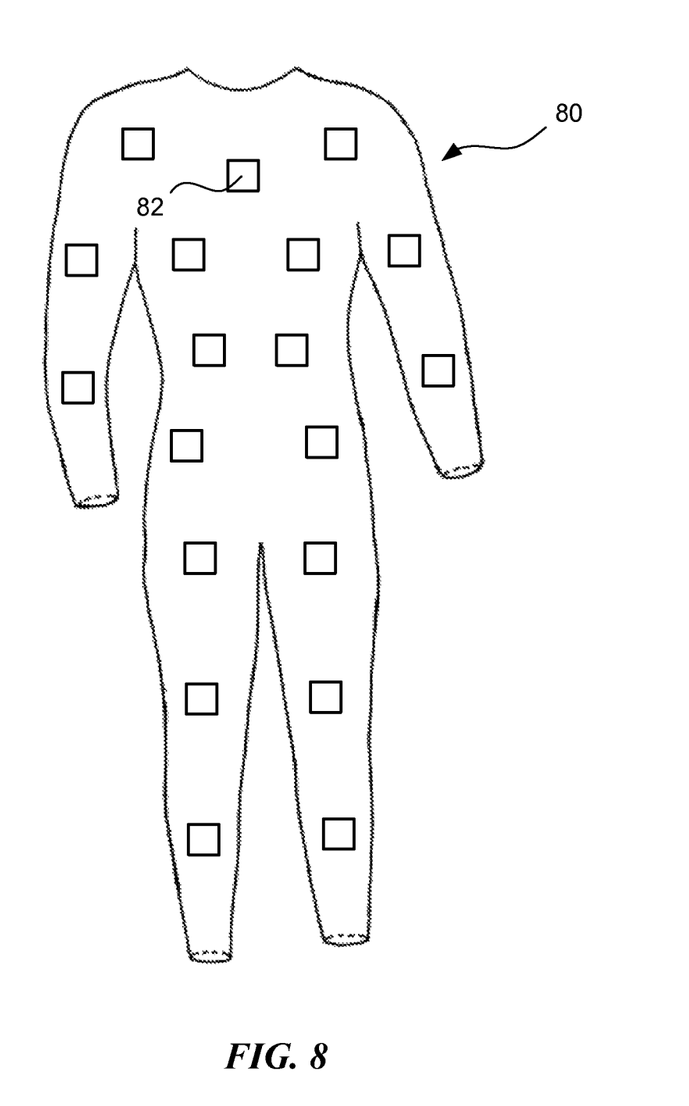
FIG. 8 is an illustration showing a garment with a plurality of patches or pockets comprising one or more radiation sensitive devices in accordance with an embodiment of the invention.

With reference now to FIG. 8, an alternative embodiment of a garment 80 is shown that includes a plurality of pockets 82 configured to contain one or more radiation detectors as described herein. As illustrated in FIG. 8, the pockets 82 can be located at various positions on the garment relative to particular parts of the body. In some cases, the pockets can include wiring to make an electrical connection to the one or more radiation detectors within the pockets, and the garment can include wiring to electrically connect the radiation detectors to an external port for attachment to a computer or electrical device to monitor the electrical signals generated from the radiation detectors as result of incident radiation. In other embodiments, the radiation sensitive devices are self-contained, i.e., they include components for detecting radiation and storing the electrical signals generated by the incident radiation, as well as a power source to operate the detector. In some cases, the self-contained radiation detectors can be removed from the pockets and connected to a computer or other device to upload the radiation measurements from the detector for monitoring exposure of various parts of the individual's body.

III. Methods of Measuring Radiation Exposure

Figure 9:
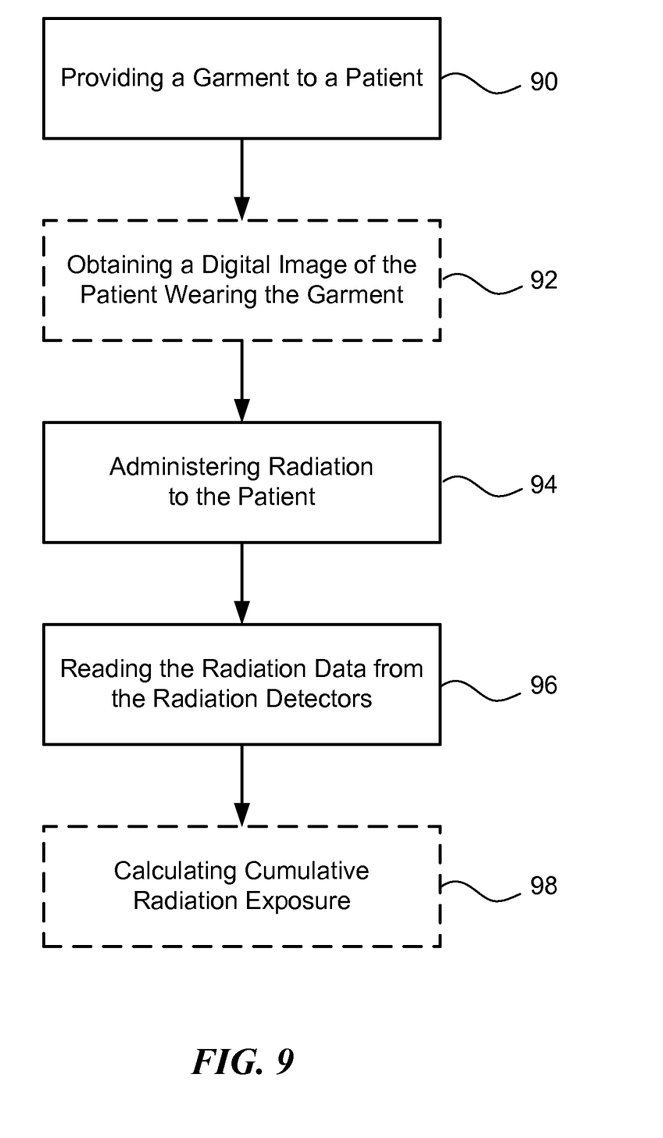
FIG. 9 is an illustration showing an exemplary flow of events in a method for monitoring radiation exposure and optionally calculating a cumulative exposure in accordance with an embodiment of the invention.

With reference now to FIG. 9, a flowchart illustrating a series of steps for monitoring radiation exposure is shown. In the illustrated embodiment, the method includes providing a garment, as discussed herein, to a patient 90, optionally obtaining a digital image of the patient wearing the garment 92, administering radiation to the patient 94, reading the radiation data from the radiation detectors 96, and optionally calculating cumulative radiation exposure 98. In embodiments of the method that include obtaining a digital image of the patient wearing the garment, the image can be obtained before, during or after exposure to the radiation. In some cases, the image is obtained before, and the markers that are visible in the image and used to correlate radiation dose to particular parts of the body are removed prior to administration of the radiation.

In some cases, the radiation data can be analyzed, e.g., via computer software, to calculate the distribution of radiation dose over the patient's entire body, or part thereof. The dose received for any particular treatment or diagnostic session can be combined with previously stored information, e.g., on the computer and accessible via the computer software, to calculate a cumulative radiation dose over the patient's entire body, or part thereof. In some cases, computer software can be used to generate an image of a virtual human body, to illustrate the session dose or cumulative dose at one or more body parts or for the entire body. The computer software can also generate session dose or cumulative dose information in tabular or graphical form for one or more particular body parts or for the entire body. Additional information regarding the geometry of the source and/or the energy of the incident radiation can also be generated from the data collected at various detectors.

All references cited herein, including patents, patent applications, and publications, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A garment, comprising:
   an array of radiation sensitive devices; and
   a fabric-based flexible circuit electrically coupled to the array of radiation sensitive devices,
   wherein the garment is shaped to be worn by an individual, to cover all or substantially all of the individual's body or part thereof, and to fit snugly against the individual's body when worn, such that the radiation sensitive devices correlate to specific one or more locations of the individual's body, and
   wherein the radiation sensitive devices are configured to measure doses of radiation incident upon the specific one or more locations of the individual's body.

2. The garment of claim 1, wherein the garment is shaped to cover the individual's entire body excluding the face, hands and feet.

3. The garment of claim 1, wherein the garment is in the shape of a T-shirt and covers the individual's torso.

4. The garment of claim 3, wherein the garment is shaped to further cover the individual's arms.

5. The garment of claim 1, wherein the garment is in the shape of shorts and covers the individual's pelvis, or is in the shape of pants and covers the individual's pelvis and legs.

6. The garment of claim 1, wherein the fabric-based flexible circuit comprises a conductive ink printed on a polymer or nylon fabric in a predetermined circuit pattern.

7. The garment of claim 1, wherein the fabric-based flexible circuit comprises a fabric substrate that is substantially transparent to ionizing radiation.

8. The garment of claim 1, wherein each radiation sensitive device is from 25 $\mu m^2$ to 2.5 $mm^2$ in size.

9. The garment of claim 8, wherein each radiation sensitive device is from 250 $\mu m^2$ to 1 $mm^2$ in size.

10. The garment of claim 1, wherein the radiation sensitive devices comprise MOSFET, RADFET or IGFET semiconductor components.

11. The garment of claim 1, wherein the radiation sensitive devices comprise flat panel detectors.

12. The garment of claim 1, wherein the array comprises at least one device per 100 $cm^2$.

13. The garment of claim 1, wherein the array comprises at least one device per 25 $cm^2$.

14. The garment of claim 1, further comprising a plurality of markers positioned at predetermined locations relative to the array of devices.

15. The garment of claim 14, wherein the markers are identifiable in a digital image of the garment when worn by the individual.

16. The garment of claim 1, wherein the array and the flexible circuit form an integrated internal layer, and further comprising an external layer connected to the internal layer to form an inflatable space there between, wherein the space can be inflated with air when worn by the individual.

17. The garment of claim 1, further comprising a data collection device electrically coupled to the flexible circuit to receive and store radiation data.

18. A garment, comprising:
a plurality of pockets;
a plurality of radiation sensitive devices contained in the plurality of pockets; and
a plurality of markers located on the garment in positions relative to portions of an individual's body when the garment is worn and relative to the radiation sensitive devices to correlate the location of the radiation sensitive devices to portions of the individual's body,
wherein the garment is shaped to be worn by the individual, to cover all or substantially all of the individual's body or part thereof, and to fit snugly against the individual's body when worn such that the radiation sensitive devices correlate to specific one or more locations of the individual's body, and
wherein the radiation sensitive devices are configured to measure doses of radiation incident upon the specific one or more locations of the individual's body.

19. A method of monitoring radiation exposure in an individual undergoing a radiation diagnostic or treatment session, comprising:
supplying an individual with the garment of claim 1;
administering radiation to the individual; and
recording the radiation incident on the radiation sensitive devices.

* * * * *